(12) United States Patent
Nakahira et al.

(10) Patent No.: US 9,267,898 B2
(45) Date of Patent: Feb. 23, 2016

(54) OPTICAL INSPECTION METHOD AND OPTICAL INSPECTION APPARATUS

(75) Inventors: Kenji Nakahira, Yokohama (JP);
 Toshifumi Honda, Yokohama (JP);
 Toshihiko Nakata, Hiratsuka (JP)

(73) Assignee: HITACHI, LTD., Tokyo (JP)

( * ) Notice: Subject to any disclaimer, the term of this patent is extended or adjusted under 35 U.S.C. 154(b) by 169 days.

(21) Appl. No.: 13/983,077

(22) PCT Filed: Dec. 20, 2011

(86) PCT No.: PCT/JP2011/079558
 § 371 (c)(1),
 (2), (4) Date: Aug. 21, 2013

(87) PCT Pub. No.: WO2012/117646
 PCT Pub. Date: Sep. 7, 2012

(65) Prior Publication Data
 US 2013/0329227 A1 Dec. 12, 2013

(30) Foreign Application Priority Data
 Mar. 2, 2011 (JP) ................................. 2011-045468

(51) Int. Cl.
 *G01N 21/88* (2006.01)
 *G01N 21/956* (2006.01)
 *G01N 21/95* (2006.01)

(52) U.S. Cl.
 CPC ............ *G01N 21/88* (2013.01); *G01N 21/9501* (2013.01); *G01N 21/956* (2013.01); *G01N 2021/8835* (2013.01)

(58) Field of Classification Search
 CPC ........... G01B 11/0675; G01B 11/2441; G01B 11/30; G01B 11/306; G01B 9/0201; G01N 21/45; G01N 21/88; G01N 21/8803; G01N 21/9501; G01N 21/956; G01N 2021/8835
 USPC ............................ 356/450–521, 237.2–237.5
 See application file for complete search history.

(56) References Cited

U.S. PATENT DOCUMENTS 5,903,342 A 5/1999 Yatsugake et al.
6,524,871 B2 * 2/2003 Okawauchi ..................... 438/16
(Continued)

FOREIGN PATENT DOCUMENTS

JP 8-86746 4/1996
JP 8-304296 11/1996
(Continued)

*Primary Examiner* — Michael P Lapage
(74) *Attorney, Agent, or Firm* — Baker Botts L.L.P.

(57) ABSTRACT

An optical inspection apparatus is provided which suppresses the influence of quantum noise including: light irradiator which irradiates a sample with light; reference light emitter which emits reference light; light interference unit which generates interfering light through interference between transmitted light, scattered light, or reflected light from the sample irradiated with light by the light irradiator, and the reference light emitted by the reference light emitter; light detector which detects the interfering light generated by the light interference unit; defect identifier which identifies the presence or absence of a defect based on a detection signal obtained by the light detector detecting the interfering light; and light convertor which converts at least the state of the transmitted, scattered, or reflected light from the sample, the state of the reference light emitted by the reference light emitter, or the state of the interfering light generated by the light interference unit.

4 Claims, 12 Drawing Sheets

(56) References Cited

U.S. PATENT DOCUMENTS

| | | | |
|---|---|---|---|
| 2001/0030296 A1 | 10/2001 | Ishimaru et al. | |
| 2002/0080363 A1* | 6/2002 | Tukker | 356/484 |
| 2006/0216200 A1 | 9/2006 | Nagatomo et al. | |
| 2007/0206198 A1 | 9/2007 | Serikawa | |
| 2007/0285670 A1* | 12/2007 | Yoshida et al. | 356/489 |
| 2009/0296096 A1* | 12/2009 | Jeong | 356/450 |
| 2011/0075151 A1* | 3/2011 | Jeong | 356/453 |

FOREIGN PATENT DOCUMENTS

| | | |
|---|---|---|
| JP | 9-304289 | 11/1997 |
| JP | 2001-272603 | 10/2001 |
| JP | 2006-201179 | 8/2006 |
| JP | 2006-234693 | 9/2006 |
| JP | 2007-232667 | 9/2007 |

* cited by examiner

OPTICAL INSPECTION METHOD AND OPTICAL INSPECTION APPARATUS

BACKGROUND

The present invention relates to an optical inspection method and an optical inspection apparatus for inspecting a minute defect on the surface of a sample by irradiating the sample with light and detecting reflected light therefrom.

In the manufacturing lines of semiconductor substrates, thin film substrates and the like, optical inspection apparatuses are used extensively to inspect minute defects on the surface of samples so as to acquire a high product yield (e.g., JP-9 (1997)-304289-A (Patent Literature 1) and JP-2006-201179-A (Patent Literature 2)). Generally, the optical inspection apparatus irradiates the sample surface with a focused light beam of several tens of μm across, detects transmitted light, scattered light, or reflected light from any defect, and focuses the detected light for defect detection. Currently commercialized apparatuses can inspect defects of several tens of nm or more across.

Meanwhile, with advances in fine processing technology, there has been a growing need for inspecting defects more minute than ever. Because a minute defect gives off faintly reflected light when irradiated with illumination light, more sensitive, higher-performing defect detection technology is needed. In particular, given faint light, it is impossible to ignore the influence of fluctuation called quantum noise stemming unavoidably from the uncertainty principle of quantum mechanics. This makes it important to suppress the influence of quantum noise.

One method for detecting such minute defects, as described in JP-2007-232667-A (Patent Literature 3) for example, involves identifying the presence or absence of a defect based on information about the differences in phase and amplitude between the light obtained from the sample typically through homodyne detection or heterodyne detection on the one hand, and reference light on the other hand.

SUMMARY OF INVENTION

Conventional apparatuses use a detector first to convert the light interfering with the reference light into an electrical signal and perform defect detection on the electrical signal thus obtained. In this case, following the detection of the light by the detector, it is intrinsically impossible to suppress the influence of quantum noise. That means it is necessary to suppress the influence of quantum noise in advance. In the past, however, no conversion was performed in order to suppress the influence of quantum noise on the interference with the reference light. For this reason, when the quantity of light was small, it was impossible to obtain good defect detection performance.

The present invention aims to solve the above problem by providing an optical inspection method and an optical inspection apparatus outlined below. That is, the invention provides an optical inspection apparatus including: light irradiator which irradiates a sample with light; reference light emitter which emits reference light; light interference unit which generates interfering light through interference between transmitted light, scattered light, or reflected light from the sample irradiated with light by the light irradiator on the one hand, and the reference light emitted by the reference light emitter on the other hand; light detector which detects the interfering light generated by the light interference unit; defect identifier which identifies the presence or absence of a defect based on a detection signal obtained by the light detector detecting the interfering light; and light converter which converts at least the state of the transmitted light, scattered light, or reflected light from the sample, the state of the reference light emitted by the reference light emitter, or the state of the interfering light generated by the light interference unit.

In this manner, when the state of light is converted before the light is detected, it is possible to suppress the influence of quantum noise while improving the sensitivity of defect detection or to shorten inspection time while maintaining the sensitivity of defect detection.

Also, the present invention is characterized in that the light convertor changes the phase of the reference light in accordance with at least the required sensitivity of defect detection, required throughput, or the type of the defect to be detected.

The phase of the reference light highly impervious to the influence of quantum noise varies depending on the required sensitivity of defect detection, required throughput, or the type of the defect to be detected. This invention makes it possible to optimize the phase of the reference light in keeping with the required value.

Also, the present invention is characterized in that the light conversion unit calculates a quantum state indicative of the state of the transmitted light, scattered light, or reflected light from the sample at least either when there is a defect or when there is no defect, and changes the phase of the reference light based on that quantum state.

In this manner, when the state desired to be identified is modeled into a quantum state, it is possible suitably optimize the phase of the reference light by taking the influence of quantum noise into consideration. In this case, calculating the quantum state in effect when there is a defect can control the probability that the existing defect is accurately detected (accurate detection rate); calculating the quantum state in effect when there is no defect can control the probability that a nonexistent defect is falsely identified as the defect (false alarm rate). If the quantum state in effect when there is a defect and the quantum state in effect when there is no defect are both calculated, it is possible to perform highly appropriate detection for controlling the accurate detection rate and false alarm rate.

Also, the present invention is characterized in that the light convertor uses a photonic crystal on the reference light, the light prior to interference with the reference light, or the light stemming from interference with the reference light, in such a manner that the defect identifier will reduce the overlap between a probability distribution involving the presence of a defect and a probability distribution corresponding to the absence of any defect.

To convert the state of light in a manner reducing the overlap between the probability distribution corresponding to the presence of a defect and the probability distribution corresponding to the absence of any defect, nonlinear conversion is known to be needed. Nonlinear conversion involves letting the electromagnetic field representative of output light be not proportional to the electromagnetic field representing input light. With conventional optical media, it was difficult to obtain strong nonlinear optical effects. However, the photonic crystal under active development in recent years is known to provide powerful nonlinear optical effects. When a photonic crystal applied to an optical inspection apparatus is placed in front of its detector, it is possible to convert the state of the detected light so as to reduce the overlap between the probability distribution corresponding to the presence of a defect and the probability distribution corresponding to the absence of any defect, whereby the influence of quantum noise is suppressed.

Also, the present invention is characterized in that the light convertor uses a photonic crystal on the reference light when converting the state of the light so that the defect identifier will reduce the overlap between the probability distribution corresponding to the presence of a defect and the probability distribution corresponding to the absence of any defect.

To detect a minute defect, it is necessary to detect a faint signal from the defect included in the light scattered or reflected from the sample. However, when the state of the light is converted, the light convertor can incur considerable unintended disturbances due to such factors as material unevenness of optical media and insufficient accuracy of optical axis alignment. This invention aims not to change the state of the light including a faint signal from the defect with the light convertor, but to change the state of only the reference light using the light convertor thereby preventing a drop in performance caused by the disturbances.

Also, the present invention is characterized in that the defect identifier obtains not only the information about the presence or absence of a defect but also information about the type of the defect.

The light scattered or reflected from the sample includes information not only about the presence or absence of a defect but also about the type of the defect. In an apparatus structure similar to that for defect detection, the light convertor is used to convert the state of the light in a manner acquiring much information about the type of defect, so as to obtain the information about the defect type while suppressing the influence of quantum noise.

According to the present invention, the light convertor for converting the state of transmitted, scattered or reflected light from the sample through interference with the reference light converts the state of the light in a manner reducing the overlap between the probability distribution corresponding to the presence of a defect and the probability distribution corresponding to the absence of any defect, whereby the influence of quantum noise is suppressed and defect detection is carried out with high accuracy.

These features and advantages of the invention will be apparent from the following more particular description of preferred embodiments of the invention, as illustrated in the accompanying drawings.

DESCRIPTION OF THE PREFERRED EMBODIMENTS

The present invention relates to an optical inspection apparatus for inspecting a minute defect that may exist on the surface of a sample irradiated with light. More particularly, the invention relates to an optical inspection apparatus and an optical inspection method for suppressing the influence of quantum noise that may become problematic when the light to be detected is weak. Some embodiments of the present invention are explained below in reference to the accompanying drawings.

First Embodiment

Figure 1:
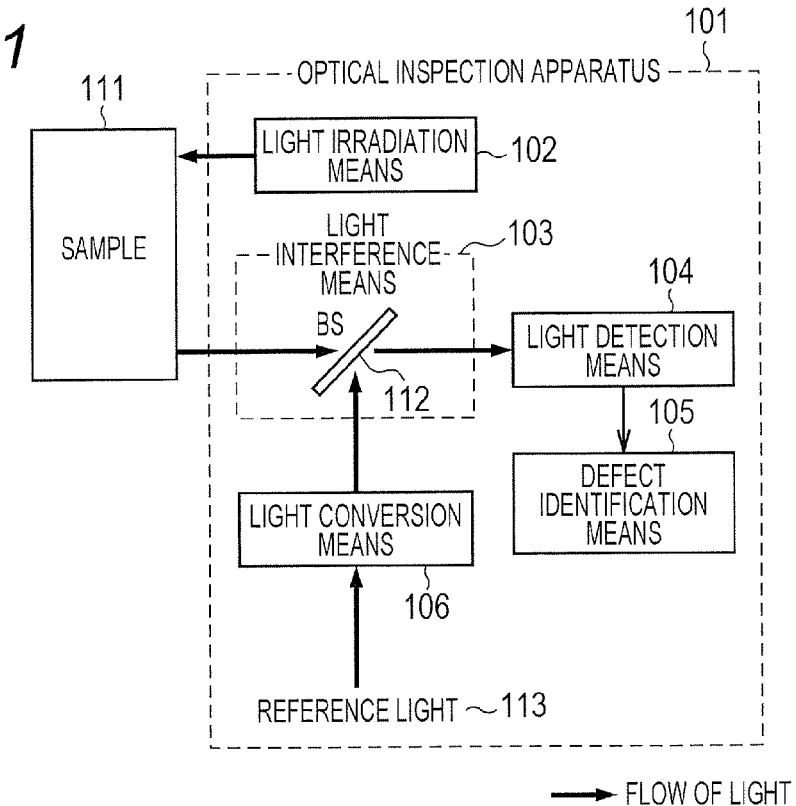
FIG. 1 is a block diagram showing an overall structure of an optical inspection apparatus as one embodiment of the present invention.

FIG. 1 shows a typical optical inspection apparatus 101 as the first embodiment that inspects a minute defect that may exist on the surface of a sample irradiated with light.

The optical inspection apparatus 101 is structured to include light irradiation means 102 for irradiating a sample 111 with light, light interference means 103 for causing the light scattered or reflected from the sample to interfere with reference light emitted by reference light source means 113, light detection means 104 for detecting the interfering light, and defect identification means 105 for identifying the presence or absence of a defect by processing a detection signal output from the light detection means 104 having detected the interfering light. The light with which the light irradiation means 102 irradiates the sample 111 is often focused onto the sample 111 so that the sample surface may be scanned with the focused light for enhancing spatial resolution. However, this is not limitative of this invention. The light interference means 103 normally uses a beam splitter (BS) 112 to let that part of the reflected light which comes from the sample 111 and which is transmitted through the beam splitter (BS) 112 interfere with that part of the reference light which is emitted by the reference light source means 113 and reflected by the beam splitter (BS) 112.

Furthermore, the optical inspection apparatus 101 includes light conversion means 106 for converting light in such a manner as to reduce the overlap between a probability distribution of detection signals corresponding to the presence of a defect on the one hand and a probability distribution of the detection signals corresponding to the absence of any defect on the other hand. In the typical structure shown in FIG. 1, the light conversion means 106 is shown located on a light path of the reference light emitted by the reference light source means 113 for converting the state of the reference light. Alternatively, the light conversion means 106 may be located on a light path of the reflected light from the sample for converting the state of the reflected light. As another alternative, the light conversion means 106 may be interposed between the light interference means 103 and the light detection means 104 for converting the state of the light stemming from the conversion.

As described above, when the state of the light prior to detection is converted, it is possible to suppress the influence of quantum noise while improving the sensitivity of defect detection or to shorten inspection time while maintaining the sensitivity of defect detection.

Incidentally, the light irradiation means 102 need only emit the type of light suitable for the purpose. For example, the light may be a laser beam having a single oscillation frequency, or a beam having multiple oscillation frequencies. The light may also be a pulse light beam that occurs intermittently, or may be continuous light. The light may be polarized in its state or may be modulated in amplitude, phase, or frequency. The light may also be in a coherent state that is the state of an ordinary laser beam. As another alternative, the light may be in a squeezed state.

Also in the structure shown in FIG. 1, the light irradiation means 102 and reference light source means 113 are separated and have an independent light sources. Alternatively, the light irradiation means 102 and reference light source means 113 may be configured to share a light source.

The light interference means 103 may be designed for interference not only with one type of reference light but also with two or more types of reference light. The type of light emitted by the reference light source 113 need not be the same as the type of light with which the light irradiation means 102 irradiates the sample 111. For example, the light irradiation means 102 may irradiates the sample with light in a coherent state while the reference light source means 113 may emit light in a squeezed state.

The light detection means 104 may have detectors arranged in array form therein to achieve higher inspection throughput. However, this is not limitative of this invention. The detection signal that is output from the light detection means 104 is usually an electrical signal. The defect identification means 105 uses an analog or digital electrical circuit to identify the presence or absence of a defect. Not only identifying the presence or absence of a defect, the defect identification means 105 may further perform processing to identify the type of the defect.

Figure 2A:
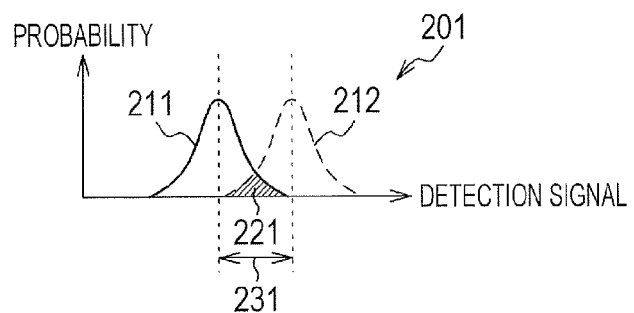
FIG. 2A shows a probability distribution in effect when light conversion means 106 for adjusting the overlap between the probability distribution corresponding to the presence of a defect and the probability distribution corresponding to the absence of any defect is not provided.
Figure 2B:
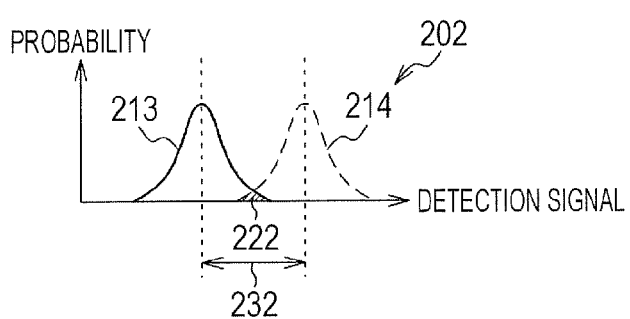
FIG. 2B is a graph showing the area of a probability distribution overlap 232 being made smaller than in a graph 201 of FIG. 2A by enlarging a mean difference 232 between probability distributions 213 and 214.
Figure 2C:
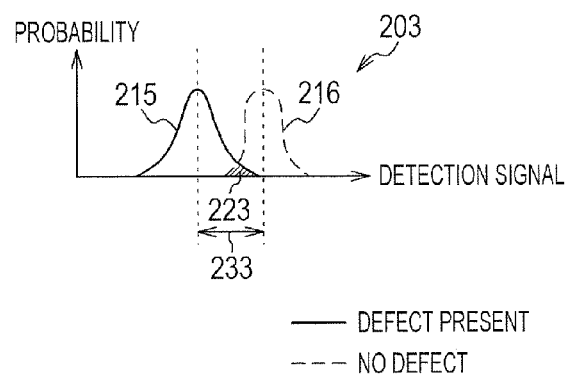
FIG. 2C is a graph showing the area of the probability distribution overlap 232 being made small by changing the shapes of the probability distributions although the mean difference 233 therebetween is the same as a difference 231 in FIG. 2A.

FIGS. 2A through 2C are each an example illustration showing the overlap between the probability distribution corresponding to the presence of a defect and the probability distribution corresponding to the absence of any defect. The graph 201 of FIG. 2A shows the probability distribution in effect when there is no optical conversion means 106 for adjusting the overlap between the probability distribution corresponding to the presence of a defect and the probability distribution corresponding to the absence of any defect. The probability distribution in effect when there is a defect is indicated by solid lines and the probability distribution in effect when there is no defect is denoted by broken lines. The horizontal axis represents a detection signal I detected by the light detection means 104, and the vertical axis denotes probability P (if the detection signals constitute continuous values, the vertical axis represents probability density). If the probability distribution is an impulse function, the detection signal has no uncertainty. In practice, however, the detection signal has an uncertainty under the influence of diverse noises. In particular, if the light to be detected is weak, the influence of the fluctuation on the light due to quantum noise can be dominant.

A probability distribution $211:P_1(I)$ in effect when there is a defect and a probability distribution $212:P_0(I)$ in effect when there is no defect have an overlap 221 therebetween. A distance 231 represents a mean difference between the probability distributions. When inspection is performed, the value of the detection signal I is determined in accordance with the probability distributions. If a prior probability in effect, when there is a defect, is equal to a prior probability in effect, when there is no defect, it may be determined that there is a defect if $P_1(x)>P_0(x)$ where x represents the acquired detection signal and that there is no defect if $P_1(x)<P_0(x)$, in order to perform defect identification involving the smallest mean error rate. Generally, prior probabilities are not equal. Furthermore, it may often be desired that defect identification be performed using other evaluation criteria (e.g., it may be desired to detect as many defects as possible while the false alarm rate is being held below a predetermined value). In any case, however, the area of the overlap 221 between the probability distributions should preferably be as small as possible.

In a graph 202 of FIG. 2B, the area of an overlap 222 between probability distributions 213 and 214 is held small by making the area of the mean difference 232 between the probability distributions larger than in the graph 201 of FIG. 2A. In a group 203 of FIG. 2C, the mean difference 233 between the probability distributions is the same as the difference 231, but the area of a probability distribution overlap 223 is kept smaller than the probability distribution overlap 221 in FIG. 2A by changing the shape of the probability distributions. In the example of the graph 203, the probability distribution 215 in effect when there is a defect is the same as the probability distribution 211, but the shape of the probability distribution 216 in effect when there is no defect is changed compared with the shape of the probability distribution 212. Also, it is possible to change the shape of the probability distribution in effect when there is a defect.

With the light conversion means 106 suitably converting the light prior to detection, it is possible to enlarge the mean difference between the probability distributions or change their shapes, or achieve both. This can reduce the overlap between the probability distributions and thereby perform defect identification with high accuracy.

Whereas the detection signal is assumed to be a scalar value in FIGS. 2A through 2C, the detection signal may also be expressed by a vector value using a plurality of detectors. For example, in the case of a commonly utilized heterodyne receiving system, the detection signal is expressed by a vector value composed of two scalar values. In the ensuing explanation, the detection signal is assumed to be a scalar value unless otherwise specified.

Figure 3:
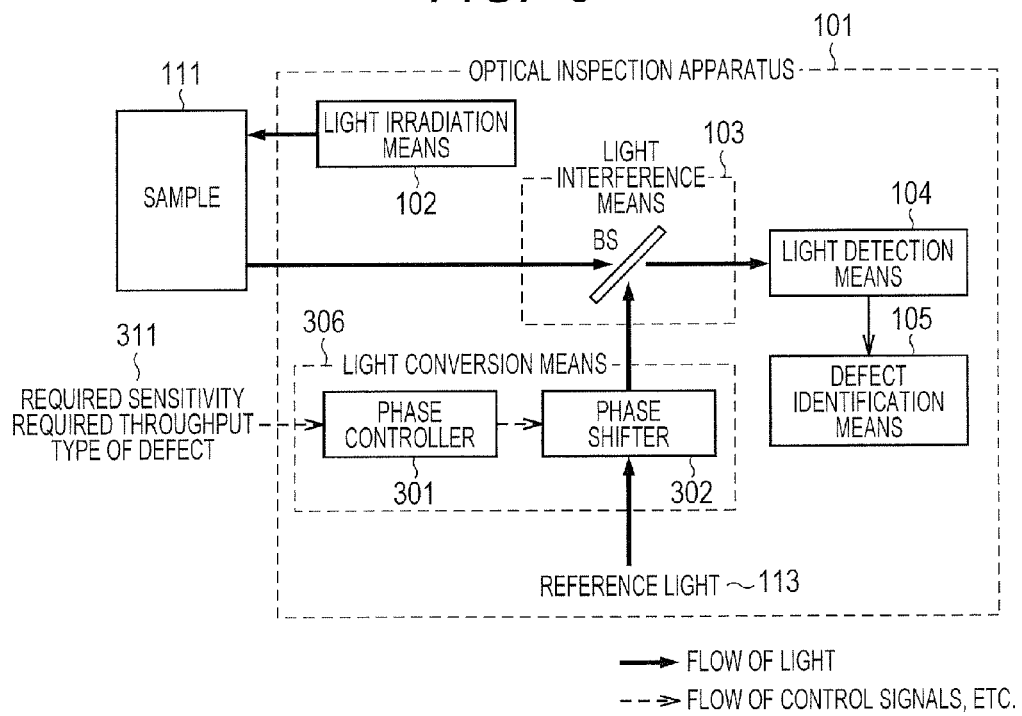
FIG. 3 is a block diagram showing an overall structure of an optical inspection apparatus including light conversion means 306 replacing the light conversion means 106 explained in FIG. 1 so that the phase of the reference light may be changed adjustably in accordance with at least the required sensitivity of defect detection, required throughput, or type of defect to be detected.

FIG. 3 is an illustration showing a structure of an optical inspection apparatus that inspects a minute defect that may exist on the surface of a sample irradiated with light. In the structure shown in FIG. 3, the light conversion means 106 explained in FIG. 1 is replaced with light conversion means 306 so as to adjustably change the phase of the above-mentioned reference light in accordance with at least the required sensitivity of defect detection, required throughput, or the type of the defect to be detected.

The same means as those in FIG. 1 are designated by the same reference numerals. In the description that follows, the same means and the same data will be designated by the same reference numerals. In the structure shown in FIG. 3, the light conversion means 306 is fed with a required value 311 representing the required sensitivity of defect detection, required throughput, or the type of the defect to be detected. The light conversion means 306 includes a phase controller 301 for controlling the phase of the reference light emitted by the reference light source means 113 and a phase shifter 302 for shifting the phase of the reference light. As will be discussed later with reference to FIGS. 7 through 10, the optimum phase of the reference light subject to interference by the light interference means 103 varies depending on required sensitivity, required throughput, or defect type. Thus the light conversion means 306 changes the phase of the reference light based on these items of information.

Changing the phase of the reference light emitted by the reference light source means 113 provides the effect of changing the mean difference between the probability distribution in effect when there is a defect and the probability distribution in effect when there is no defect. This enables defect detection in a manner maximizing the mean difference between the probability distributions, thereby suppressing the influence of quantum noise.

Incidentally, whereas the structure shown in FIG. 3 is explained as one in which the light conversion means 306 adjustably changes the phase of the reference light emitted by the reference light source means 113, the light conversion means 306 may alternatively be interposed between the light irradiation means 102 and the sample 111 so as to adjustably change the phase of the light to irradiate the sample 111 by the light irradiation means 102, whereby the phase of the reflected light from the sample 111 irradiated with light by the optical irradiation means 102 may be changed. As another alternative, the optical conversion means 306 may be interposed between the light interference means 103 and the light detection means 104 to adjustably change the phase of the light stemming from the interference.

Figure 4:
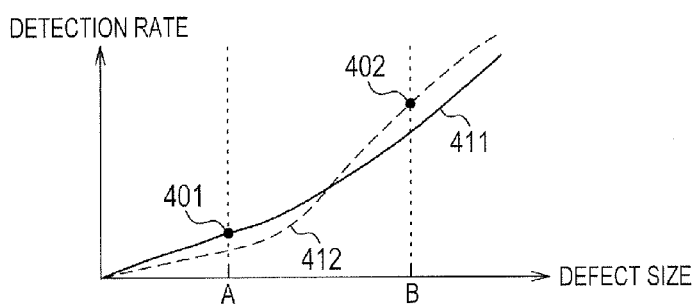
FIG. 4 is a graph showing an overall relationship between defect size and detection rate.

FIG. 4 is a graph outlining the relationship between defect size and detection rate. The horizontal axis stands for defect size and the vertical axis for detection rate. Generally, (given the same shape and the same quality of material), the larger the size of the defect, the greater the quantity of light reflected from the defect and the higher the rate of detection obtained accordingly. The graphs 411 and 412 represent the performance in effect when the phase of the reference light is adjusted to obtain the highest possible detection rate regarding defect sizes A and B, respectively. When the defect sizes are A and B, the detection rates indicated by points 401 and 402 are acquired, respectively. However, the two kinds of performance cannot go together as long as the phase of the reference light is not adjusted. Meanwhile, the required size of defect (i.e., required sensitivity) varies depending on the intended purpose. For example, it may be necessary to perform a kind of detection sensitive enough to detect defects larger than the size A, or it may be sufficient to detect defects larger than the size B.

Thus when the state of light is converted using the structures shown in FIGS. 1 and 3 in accordance with required sensitivity, it is possible to obtain performance suited for the requirement in question. Although the rate of defect detection can be raised by boosting the quantity of the light reaching the detector (light detection means 104), the quantity of light is usually increased only at the expense of throughput. By contrast, when the state of light is adjusted by the application of this embodiment for example, high sensitivity and high throughput or high detection rate can go together. Although there is a trade-off relation between required throughput and the type of the defect to be detected, it is possible to obtain good performance by suitably changing the state of light in like manner.

Figure 5A:
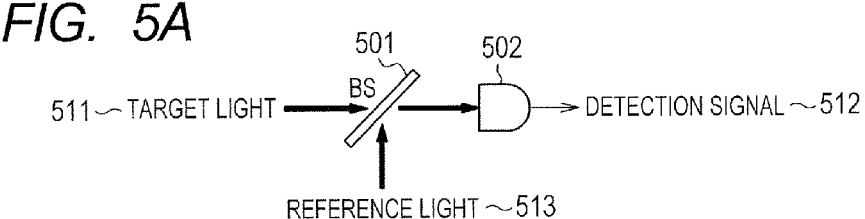
FIG. 5A is a block diagram showing a structure around the light interference means for implementing a detection method called homodyne detection.
Figure 5B:
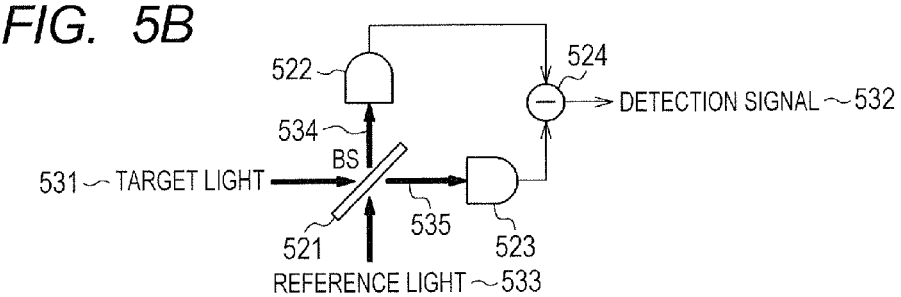
FIG. 5B is a block diagram showing a structure around the light interference means for implementing a detection method called balanced homodyne detection.
Figure 5C:
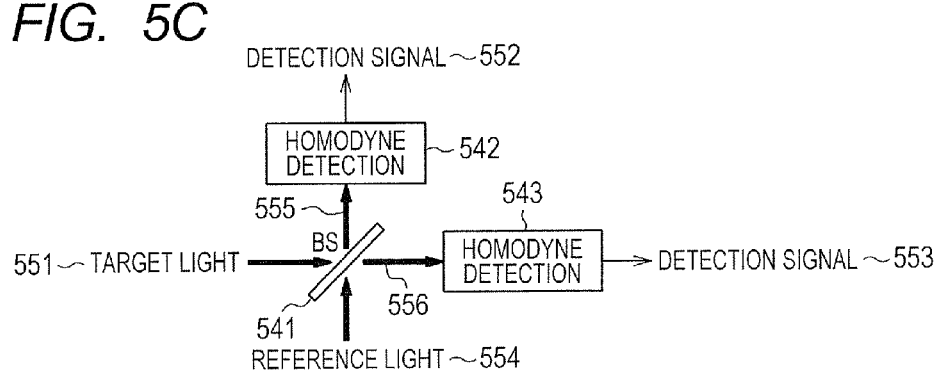
FIG. 5C is a block diagram showing a structure around the light interference means for implementing a detection method called heterodyne detection.

FIGS. 5A through 5C show variations of the light interference means 103 and light detection means 104 in FIG. 1. In the ensuing description, the reflected light from the sample 111 irradiated with light by the light irradiation means 102 will be called the target light, and the light emitted by the reference light source means 113 will be called the reference light.

FIG. 5A is an illustration showing a structure for implementing a detection method called homodyne detection. That part of target light 511 which is transmitted through a beam splitter 501 (corresponding to the beam splitter 112 in FIG. 1 or 3) and that part of reference light 513 which is transmitted through the beam splitter 501 interfere with each other. The light derived from the interference is detected by a detector 502 (corresponding to the light detection means 104 in FIG. 1 or 3) which in turn outputs a detection signal 512. The beam splitter 501 may be a polarizing beam splitter that changes its reflection rate depending on the polarized state of the light.

FIG. 5B is an illustration showing a structure for implementing a detection method called balanced homodyne detection. Target light 531 and reference light 533 are allowed to interfere with each other using a beam splitter 521 (a half beam splitter with a transmission factor of 50%). The interference light 534 and 535 are detected by detectors 522 and 523, respectively. An arithmetic unit 524 acquires the difference between the signals from the detectors and outputs a detection signal 532 accordingly.

FIG. 5C is an illustration showing a structure for implementing a detection method called heterodyne detection. Target light 551 and reference light 554 are allowed to interfere with each other using a beam splitter 541. The interference light 555 and 556 are subjected to homodyne detection 542 and 543 respectively, whereby two types of detection signals 552 and 553 are obtained. The structure explained in FIG. 5A is used to perform the homodyne detection 542 and 543.

The methods of detection explained in FIGS. 5A through 5C suppress quantum fluctuation in the reference light to let the information about the amplitude and phase of the target light appear in detection signals, so that detection signals may be used to perform defect detection.

Figure 6:
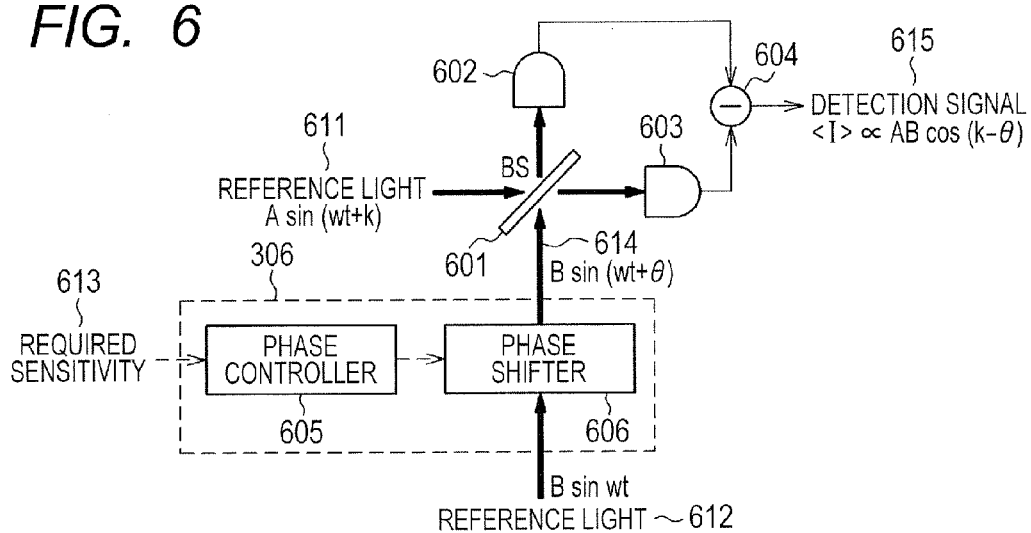
FIG. 6 is a block diagram showing a structure around the light interference means in an embodiment having light conversion means furnished with a phase shifter.

FIG. 6 is an illustration showing a typical structure in which the light interference means and light detection means explained in FIGS. 5A through 5C are supplemented with light conversion means. The structure shown in FIG. 6 combines the balanced homodyne detection system explained in FIG. 5B, with the light conversion means 306 explained in FIG. 3, the structure being capable of changing the phase of the reference light in accordance with required sensitivity.

It is assumed that a mean amplitude of target light 611 is expressed by A sin(wt+k) as a function of time t (where A(>0) is a maximum amplitude and w denotes angular frequency). It is also assumed that k=0 if there is no defect and k=α if there is a defect; the phase k of the target light is assumed to vary depending on the presence or absence of a defect. It should be noted that the amplitude of the target light includes fluctuation caused by quantum noise or the like. Thus what is desired here is to estimate the phase k from the detection signal to identify the presence or absence of a defect. It is assumed that the mean amplitude of the reference light is expressed by B sin(wt) (B>0). A phase shifter 606 under control of a phase controller 605 fed with required sensitivity 613 is assumed to convert reference light 612 into B sin(wt+θ) such as light 614. The target light 611 and the reference light 614 controlled in phase by the phase shifter 606 are each half reflected by and half transmitted through a half beam splitter 601 that produces two flows of interfering light. The two flows of interfering light are detected by detectors 602 and 603, respectively. The outputs from the detectors 602 and 603 are input to an arithmetic unit 604 for computation, the arithmetic unit 604 in turn outputting a detection signal 615. In this case, performing balanced homodyne detection causes a mean value <I> of detection signals I to be proportional to AB cos(α−θ). Since θ is already known, measuring the product of AB beforehand allows the phase k of the target light to be estimated.

Figure 8:
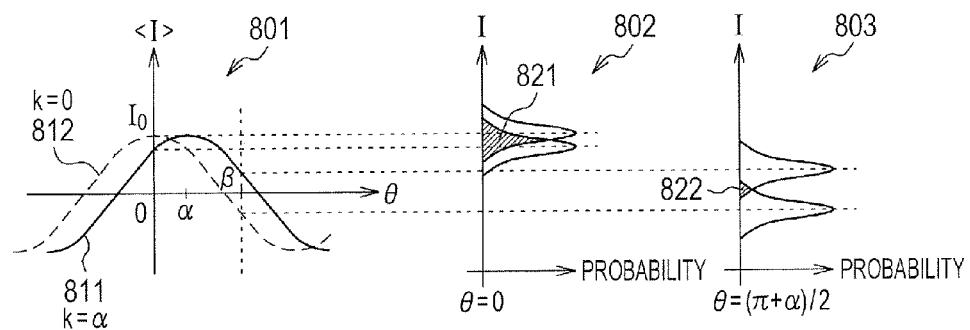
FIG. 8 is a set of graphs showing mean values of detected signals and their probability distributions, the signals indicating that the influence of quantum noise can be suppressed by changing the phase of the reference light.

Next, FIG. 8 is used to show that the phase θ of the reference light needs to be set for a suitable value in order to suppress the influence of quantum noise in the example of FIG. 6. Consider a case of very faint light in which quantum noise is dominant. A graph 801 is an illustration indicating relations between a phase shift amount θ of the reference light 612 in FIG. 6 and a mean value <I> ∝ cos(α−θ) of detection signals. A graph 811 and a graph 812 apply when there is a defect (k=α) and when there is no defect (k=0), respectively. In this example, the relation $0 \leq \alpha \leq \pi/2$ is held.

A graph 802 shows a probability distribution of detection signals I where k=0 or α on the assumption that θ=0. The mean value <I> of the detection signals is $I_\theta$ when k=0 and $I_\theta \cos\alpha$ when k=α, the difference therebetween being $I_\theta(1-\cos\alpha)$. Because quantum noises overlay with one another, the probability distribution of the detection signals I has a certain width. In the case of coherent light, the variance of the detection signals I is proportional to $I_\theta$ and is not dependent on θ or α. In the graph 802, a hatched region 821 represents the overlap between the probability distribution corresponding to the presence of a defect and the probability distribution corresponding to the absence of any defect.

A graph 803 shows the probability distribution of the detection signals I in effect when $\theta=(\pi+\alpha)/2$ is set. The mean value <I> of the detection signals is $I_\theta \cos((\pi+\alpha)/2)$ when k=0 and $I_\theta \cos((\pi-\alpha)/2)$ when k=α, the difference therebetween being larger than when the setting is θ=0. Since the variance of the measured values is the same as when θ=0, an overlap 822 between the probability distribution corresponding to the presence of a defect and the probability distribution corresponding to the absence of any defect is smaller than in the case of θ=0.

It can be seen from the above that the size of the overlap between the probability distribution corresponding to the presence of a defect and the probability distribution corresponding to the absence of any defect can be changed using the value θ. It is possible to set θ for an appropriate value using the state of light estimated when there are defects and the state of light estimated when there is no defect. Although the light in the above example is assumed to be coherent light, the same argument holds for squeezed light or other states of light.

Figure 7A:
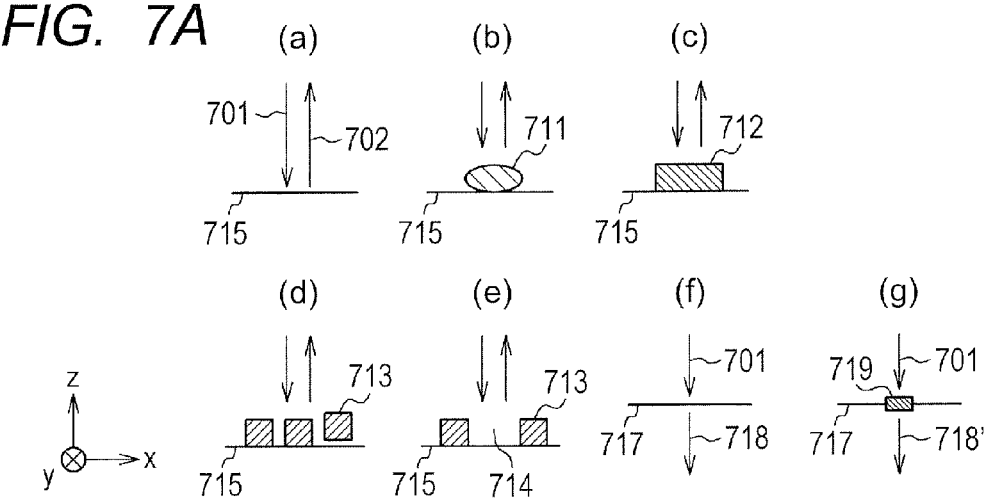
FIG. 7A is a set of cross-sectional views of patterns or defects, showing typical shapes and types of the defects.

FIG. 7A shows typical shapes and types of defects. Subfigure (a) shows a typical sample 715 positioned to be free of defects. An arrow 701 indicates light applied to the sample, and an arrow 702 denotes reflected light from the sample. Subfigure (b) shows a typical sample that includes a defect 711. Irradiation light 701 hits the defect 711, generating target light 702 that is reflected light including scattered light from the defect 711. The length of the light path is different from the case in Subfigure (a) by the height of the defect, so that the phase of the target light 702 differs from that of the case in Subfigure (a). Subfigure (c) shows a typical sample including a defect 712 which has the same height as the defect 711 but which has a different cross-sectional shape. Since the defect 711 in Subfigure (b) has the same height as the defect 712 in Subfigure (c), the light path length is the same for both. But when the type and shape of the sample is different, the way the sample and light interact with each other changes, which generally entails varying the amplitude and phase of the target light. Subfigure (d) shows a typical sample positioned to be free of defects but different from the example in Subfigure (a). In this example, the sample 715 is shown having a convexo-concave pattern 713 formed thereon but with no defect. Subfigure (e) is an example in which the sample 715 has the convexo-concave pattern 713 formed thereon including a defect 714 as part of the pattern. A part of the convexo-concave pattern 713 is missing, which constitutes one type of defect. Since the sample in Subfigure (e) differs from the defect-free sample 715 in Subfigure (d) in terms of light path length and in the way the sample and light interact with each other, the case in Subfigure (e) also affects the amplitude and phase of the target light 702. Subfigure (f) shows a typical example 717 positioned to be free of defects. In this example, transmitted light 718 from the sample 717 is the target light. Subfigure (g) shows a typical sample 717 that includes a defect 719. The defect 719 changes the state of transmitted light 718'. Depending on the sample to be inspected and the type of defect, the target light is constituted either by the transmitted light from the sample or by the reference light or reflected light. In any case, there occurs a change between the state of the target light in effect when there are defects and the state of the target light in effect when there is no defect. If that change can be detected, the presence or absence of a defect can be identified accordingly.

Figure 7B:
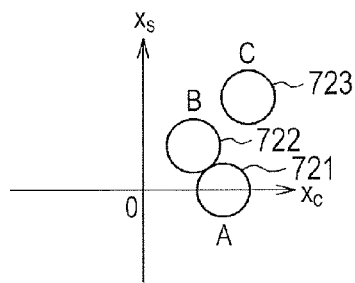
FIG. 7B is a graph as a typical phase space representation indicating the state of the target light in effect when there is a defect and the state of the target light in effect when there is no defect, the target light fluctuating isotropically on an $x_c$ axis and on an $x_s$ axis.
Figure 7C:
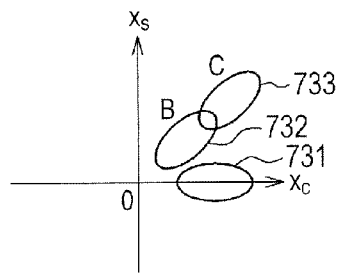
FIG. 7C is a graph as a typical phase space representation indicating the state of the target light in effect when there is a defect and the state of the target light in effect when there is no defect, the target light fluctuating differently on the $x_c$ axis and on the $x_s$ axis.

FIGS. 7B and 7C are each a typical phase space representation indicating states of target light. The distance from the origin represents the amplitude of the target light, and the angle relative to an $x_c$ axis denotes the phase of the target light. If noises do not overlap with one another and if the amplitude and phase take only fixed values, then the state of the light is expressed by a single point in the phase space representation. In practice, quantum noise inevitably intervenes, which renders the amplitude and phase uncertain. The state of the light with such uncertainty is expressed by a probability density distribution in a two-dimensional space defined by $(x_c, x_s)$ coordinates. Here, regions with probabilities higher than a predetermined value are indicated by circles and ellipses.

In FIG. 7B, a region 721 represents the state of the target light 702 in effect when there is no defect (e.g., the case of Subfigure (a) in FIG. 7A). A region 722 denotes the state in effect when there is a defect (e.g., the case of Subfigure (b) in FIG. 7A). Compared with the region 721, the mean amplitude of the target light 702 (i.e., distance from origin O to the center of each of the regions) is the same but the mean phase of the target light 702 (i.e., the angle between a line connecting origin O with the center of each region on the one hand and the $x_c$ axis on the other hand) is different. A region 723 represents the state in effect when there is a defect different from that of the region 722 (i.e., the state of Subfigure (c) in FIG. 7A). Compared with the region 722, the mean amplitude of the target light 702 is also different. FIG. 7C shows an example in which the sample is irradiated with light whose state is different from that in FIG. 7B. As shown in this example, the state of the target light 702 may or may not have isotropic fluctuations on the $x_c$ axis and $x_s$ axis. The target light 702 reflected from the sample 715 irradiated with light in a coherent state used as the irradiation light 701 often incurs isotropic fluctuations on the $x_c$ axis and $x_s$ axis as shown in FIG. 7B. Where light in a squeezed state is used as the irradiation light 701, the target light 702 incurs a large fluctuation on the $x_c$ axis but can suppress fluctuations on the $x_s$ axis as in a region 731. Likewise, when there are defects, the target light can be made to have fluctuations with properties such as those of regions 732 and 733. When light other than in a coherent state is used as the irradiation light 701, it is possible to suppress the overlap between the probability distribution corresponding to the presence of a defect and the probability distribution corresponding to the absence of any defect and thereby to perform defect identification with higher accuracy than before.

Figure 9A:
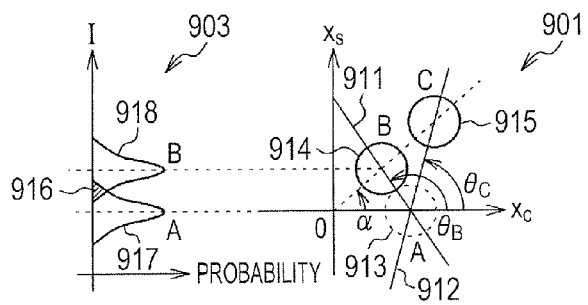
FIG. 9A is an illustration using a phase space representation showing a typical method for obtaining an appropriate amount of phase shift of the reference light.
Figure 9B:
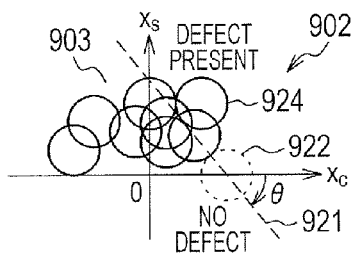
FIG. 9B is an illustration using a phase space representation showing a typical method for obtaining an appropriate amount of phase shift of the reference light, where a dotted line area 922 indicates the state of the target light in effect when there is no defect, and where solid line areas 923 indicate the state of the target light in effect when there is a defect.
Figure 9C:
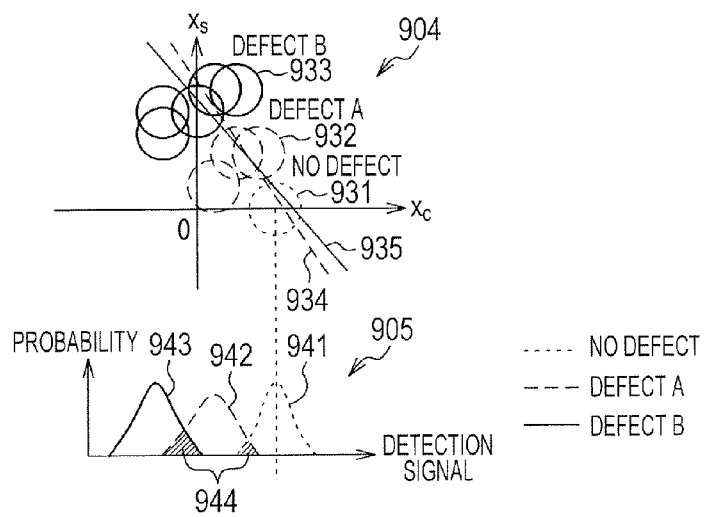
FIG. 9C has a graph 904 as an illustration using a phase space representation showing a typical method for obtaining an appropriate amount of phase shift of the reference light, where a dotted line area 931 indicates the state of the target light in effect when there is no defect, where broken like areas 932 indicate the state of the target light in effect when there is a defect and the type of the defect is type A, and where solid line areas 933 indicate the state of the target light in effect when there is a defect and the type of the defect is type B.

FIGS. 9A through 9C are illustrations based on the phase space representations explained in FIGS. 7B and 7C, each illustration showing a typical method for obtaining an appropriate phase shift amount θ of the reference light 614 in the structure of FIG. 6. A graph 901 in FIG. 9A is the phase space representation explained in FIG. 7B. The probability distribution of detection signals is obtained by projecting onto a given straight line the probability distribution expressed in a two-dimensional space defined by the $x_c$ and $x_s$ axes. For example, a graph 903 shows a probability distribution projected onto a straight line parallel to the $x_s$ axis. Probability distributions 917 and 918 correspond to the projections of regions 913 and 914, respectively. In this case, the phase shift amount θ is expressed by the angle relative to the $x_c$ axis. It can be seen that in order to reduce an overlap 916 between the probability distributions, they need only be projected onto a straight line such as a line 911 at an angle of $\theta_B$ to the $x_c$ axis. If the mean amplitude of the target light is the same between the probability distribution corresponding to the presence of a defect and the probability distribution corresponding to the absence of any defect, the expression $\theta_B(\pi+\alpha)/2$ holds, which coincides with the optimum value $\theta$ explained in FIG. 8.

Consider a case of another defect of which the state is expressed by a region 915 in FIG. 9A. It can be seen in this case that in order to reduce the overlap between the probability distributions obtained by projecting the regions 913 and 915 onto a straight line, a straight line such as a line 912 need only be selected. In this example, the mean phase of the target light representing the regions 915 and 914 is the same but the mean amplitude involved is different. Here, the angle $\theta_C$ of the straight line 912 relative to the $x_c$ axis is different from $\theta_B$. In this manner, it will be understood that the optimum phase shift amount $\theta$ varies depending not only on the mean phase but also on the mean amplitude of the target light.

A graph 902 in FIG. 9B is an example different from the graph 901 in FIG. 9A. A dotted light region 922 represents the state of the target light in effect when there is no defect, and a solid line region 923 denotes the state of the target light in effect when there are defects. If the size, shape, or type of the defect to be detected is not known beforehand, the probability distribution of the amplitude and phase in effect where there are defects can be complicated in shape (expressed by a plurality of circles in the graph 902). In this case, too, the phase shift amount $\theta$ of the reference light is desired to be set appropriately. One method for setting the amount may involve obtaining a straight line 921 that separates as much as possible the state of the target light indicative of the defect most difficult to detect among all conceivable defects, from the state indicated by the region 922, and calculating the angle $\theta$ formed between the straight line and the $x_c$ axis. Defects indicated by regions other than the region 924 are detected with a higher rate than the defect indicated by the region 924, so that an overall high rate of defect detection can be achieved.

Another setting method may involve accurately obtaining the probability distribution in effect when the state indicated by the region 923 in the presence of a defect is projected onto a straight line corresponding to various phase shift amounts, and calculating the phase shift amount of the reference light in such a manner as to reduce the overlap between the acquired probability distribution and the probability distribution corresponding to the state indicated by the region 922. Because the phase shift amount is an amount to be calculated before the sample is irradiated with light, usually it is not necessary to calculate the amount at high speed; some time may be spent calculating the amount. In calculating the phase shift amount of the reference light, the frequency with which a detectable defect is detected and the importance of detecting such defects may be taken into consideration.

The graph 904 in FIG. 9C is an example different from the graph 901 in FIG. 9A or from the graph 902 in FIG. 9B. A dotted line region 931 indicates the state of the target light in the absence of a defect, a broken line region 932 denotes the state of the target light in effect when the type of defect is defect A, and a solid line region 933 represents the state of the target light in effect when the type of defect is defect B. It is assumed that the projection made onto a solid straight line 935 makes it possible to identify with utmost accuracy the presence or absence of a defect against the criteria of a mean error rate. If it is desired to identify not only the presence or absence of a defect but also the type of the defect with high accuracy, it is necessary to obtain a probability distribution 941 in the absence of a defect and probability distributions corresponding to different defect types (probability distributions 942 and 943 are shown corresponding to the defects A and B respectively) and to examine the overlap between the distributions. The phase shift amount of the reference light may then be obtained in a manner reducing the overlap 944 between these probability distributions. For example, when the projection is made onto a broken straight line 934 in the graph 904 of FIG. 9C, the presence or absence of defects and the types of defects can be identified with utmost accuracy against the criteria of the mean error rate. The straight line 934 has a phase shift amount different from that of the straight line 935 that is optimized generally without consideration for identifying the defect type. In this manner, by obtaining probability distributions for different defect types and by converting the state of light in a manner reducing the overlap between the distributions, it is possible to identify the presence or absence of a defect and the type of the defect with high accuracy.

To represent the distribution of the amplitude and phase of target light requires expressing the state of the light in a quantum state. As an expression of the quantum state corresponding to the phase spatial representation such as this example, there exists a c-number function $F(z, z^*)$ is a complex conjugate) defined on a complex plane z such as Wigner function or Glauber's P-function. Another expression of the quantum state may be a (set of) wave function or a semidefinite positive operator in a complex Hilbert space, among others. When the state of the target light is expressed in the form of a quantum state, the fluctuations of the amplitude and phase involved can be obtained. It is then possible to calculate the probability distribution in effect when there are defects and the probability distribution in effect when there is no defect and the overlap therebetween.

Modeling the state desired to be identified into a quantum state makes it possible to calculate the appropriate method for light conversion. For example, the phase of the reference light may be appropriately optimized by taking the influence of quantum noise into consideration. In this case, calculating the quantum state in effect when there is a defect can control the probability of accurately detecting a defect that may exist (accurate detection rate); calculating the quantum state in effect when there is no defect can control the probability of mistakenly recognizing a defect that does not exist (false alarm rate). When the quantum state in effect when there is a defect and the quantum state in effect when there is no defect are both calculated, it is possible to control accurate detection rate and false alarm rate so that highly appropriate detection can be accomplished.

Figure 10:
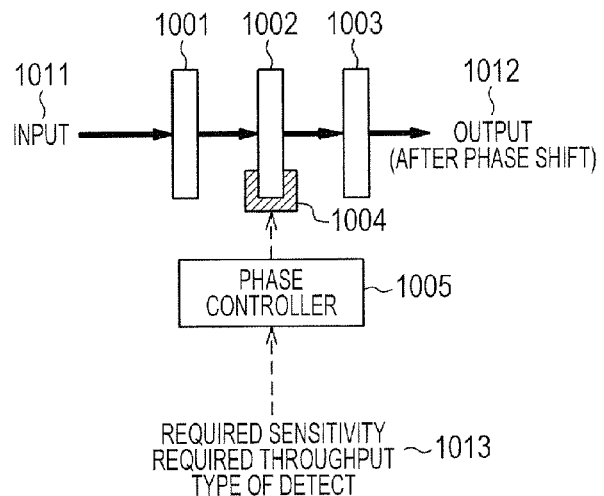
FIG. 10 is a block diagram showing an overall structure of a phase shifter that changes the phase shift amount of light.

FIG. 10 is an illustration showing a typical structure of a phase shifter (corresponding to 302 in FIGS. 3 and 606 in FIG. 6) that changes the phase shift amount of light. First, the reference light 113 (FIG. 3) or 612 (FIG. 6) that constitutes input light 1011 enters a ¼-wavelength plate 1001. Then, the light transmitted through the ¼-wavelength plate 1001 enters a ½-wavelength plate 1002 and a ¼-wavelength plate 1003, in that order. The light transmitted through the ¼-wavelength plate 1003 becomes output light 1012 from the phase shifter. The three wavelength plates 1001 through 1003 are each made of an anisotropic material. Each wavelength plate is cylindrical in shape, and light passes through its central axis. The input light is assumed to be polarized. In this structure, rotating the ½-wavelength plate shifts the phase of the input light in accordance with the angle relative to the polarizing direction of the input light. Thus a rotator 1004 for rotating the ½-wavelength plate is provided and controlled by a phase controller 1005 in accordance with required values 1013 such as required sensitivity, whereby the phase of the light can be changed in keeping with required sensitivity and other requirements.

The phase shifter that changes the phase shift amount of light may have a structure different from that of the working example shown in FIG. 10. For example, a method using a liquid crystal modulator, a method using a MEMS modulator, or a method using a variable optical delay line may be adopted instead.

Second Embodiment

Explained below in reference to FIGS. 11A through 16 are examples formed by use of nonlinear conversion means as the light conversion means 106 in the structure shown in FIG. 1.

FIGS. 11A through 11D are illustrations each showing an example in which the light conversion means 106 shown in FIG. 1 is replaced with light conversion means that converts the state of target light, reference light, or light derived from interference between the target light and reference light through nonlinear conversion using a photonic crystal. Nonlinear conversion is a type of conversion whereby the electromagnetic field representing output light is not proportional to the electromagnetic field representative of input light. The photonic crystal is a structure in which materials of different refractive indexes are cyclically arrayed. As such, the structure is known to provide properties not available with conventional optical devices. In particular, using the photonic crystal permits fabrication of a device having strong nonlinearity. By utilizing this property, it is possible to perform defect detection while suppressing the influence of quantum noise.

Figure 11A:
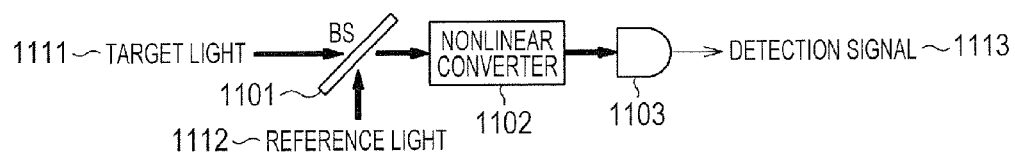
FIG. 11A shows a structure for supporting homodyne detection, in which a nonlinear transducer using a photonic crystal performs nonlinear conversion on the light stemming from interference between the target light and the reference light in the light interference means, and in which interfering light derived from the nonlinear conversion is detected using a detector.

FIG. 11A shows an example in which a nonlinear converter 1102 is used to perform nonlinear conversion on the light derived from interference between target light 1111 and reference light 1112 by light interference means 1101 and in which a detector 1103 detects the interfering light stemming from the nonlinear conversion before outputting a detection signal 1113. This is a structure corresponding to the homodyne detection explained in FIG. 5A.

Figure 11B:
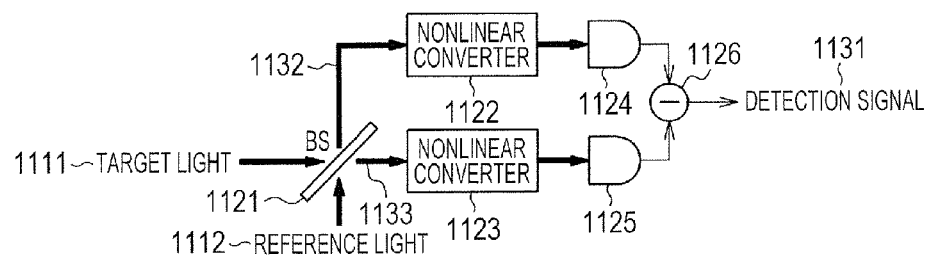
FIG. 11B is an illustration of a typical structure for supporting balanced homodyne detection, in which the target light and the reference light following interference by the light interference means are each nonlinearly converted by a nonlinear converter using a photonic crystal, in which beams of interfering light from the converters are detected using detectors, and in which the difference between output signals from the detectors is calculated using an arithmetic unit.

FIG. 11B is an illustration showing an example as a structure corresponding to the balanced homodyne detection explained in FIG. 5B, where the target light 1111 and reference light 1112 result in light beams 1132 and 1133, respectively, through interference by light interference means 1121; where the light beams 1132 and 1133 are subjected to nonlinear conversion by nonlinear converters 1122 and 1123, respectively, which output interfering light beams to be detected in turn by detectors 1124 and 1125, and where the difference between output signals from the detectors 1124 and 1125 is calculated using an arithmetic unit 1126, the result of the calculation being output as a detection signal 1131.

Figure 11C:
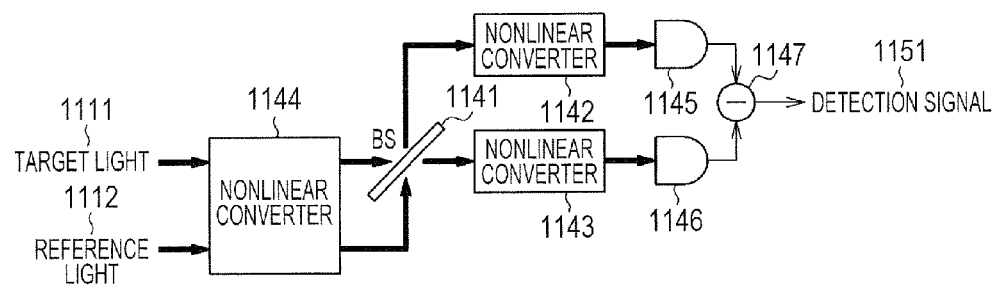
FIG. 11C is an illustration of a typical structure for supporting balanced homodyne detection, in which the structure of FIG. 11B is supplemented with a structure for performing nonlinear conversion on the target light and on the reference light.

FIG. 11C shows an example as another structure corresponding to the balanced homodyne detection explained in FIG. 5B. Compared with the structure in FIG. 11B, this example involves performing nonlinear conversion further on the target light 1111 and reference light 1112. It is not mandatory to have one beam of light input to a nonlinear converter 1144 and one beam of light output therefrom (i.e., a one-input one-output setup). In the example shown in FIG. 11C, the target light 1111 and reference light 1112 are input to the nonlinear converter 1144 which in turn outputs two beams of light that interfere with each other through light interference means 1141. The processing downstream of the light interference means 1141 is the same as that explained in FIG. 11B and thus will not be discussed further.

Figure 11D:
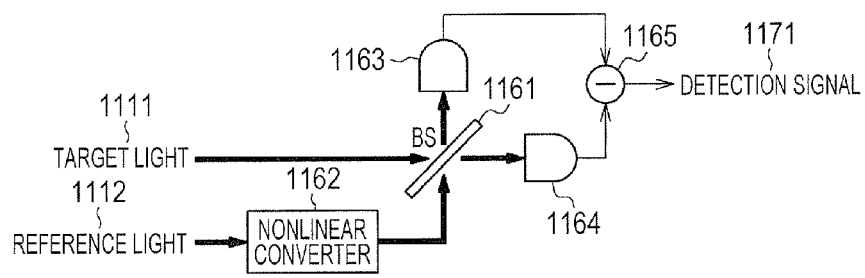
FIG. 11D is an illustration of a typical structure for supporting balanced homodyne detection, in which nonlinear conversion is performed on the reference light.

FIG. 11D shows an example as another structure corresponding to the balanced homodyne detection explained in FIG. 5B, where the reference light 1112 is subjected to nonlinear conversion by a nonlinear converter 1162. The processing downstream of light interference means 1161 is the same as that explained in FIG. 5B and thus will not be discussed further.

Nonlinear conversion is known to be needed when the state of light is to be converted in such a manner as to reduce the overlap between the probability distribution corresponding to the presence of a defect and the probability distribution corresponding to the absence of any defect. Whereas it was difficult to obtain strong nonlinear optical effects with conventional optical media, the photonic crystal under active development in recent years is known to provide powerful nonlinear optical effects. When the photonic crystal applied to the optical inspection apparatus is placed in front of its detector, it is possible to convert the state of the detected light so as to reduce the overlap between the probability distribution corresponding to the presence of a defect and the probability distribution corresponding to the absence of any defect, whereby the influence of quantum noise is suppressed.

In order to detect a minute defect, it is necessary to detect a faint signal from the defect included in the target light. However, when the state of the light is converted by the optical conversion means, such factors as material unevenness of optical media and insufficient accuracy of optical axis alignment can incur considerable unintended disturbances in the light. This invention aims not to change the state of the target light including a faint signal from the defect with the light conversion means, but to change the state of only the reference light using the light conversion means, thereby preventing a drop in performance caused by the disturbances.

In FIG. 11, there were explained structures in which nonlinear conversion is performed on the target light, the reference light, or light derived from interference between the target light and the reference light where homodyne detection is carried out. As another example, similar nonlinear conversion may also be performed where heterodyne detection or some other type of detection is carried out.

Figure 12A:
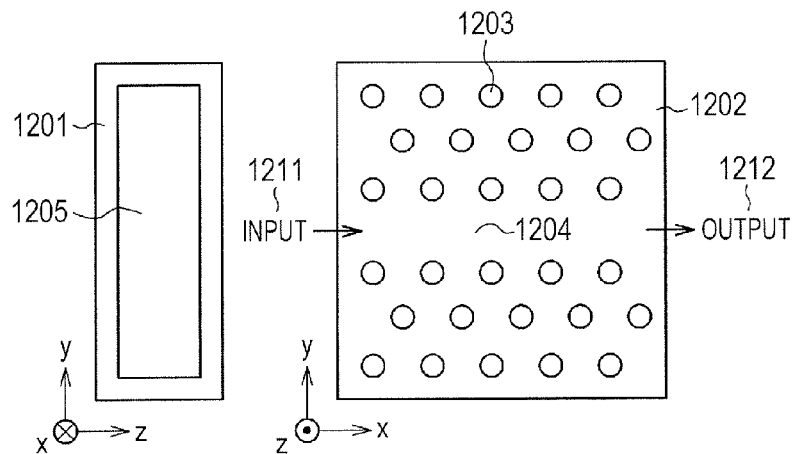
FIG. 12A is an illustration of a typical photonic crystal structure in which regions of different reflective indexes are arrayed periodically and into which a periodicity-disturbing constitution is intentionally introduced, the photonic crystal structure thereby implementing the function of a waveguide and that of light containment.
Figure 12B:
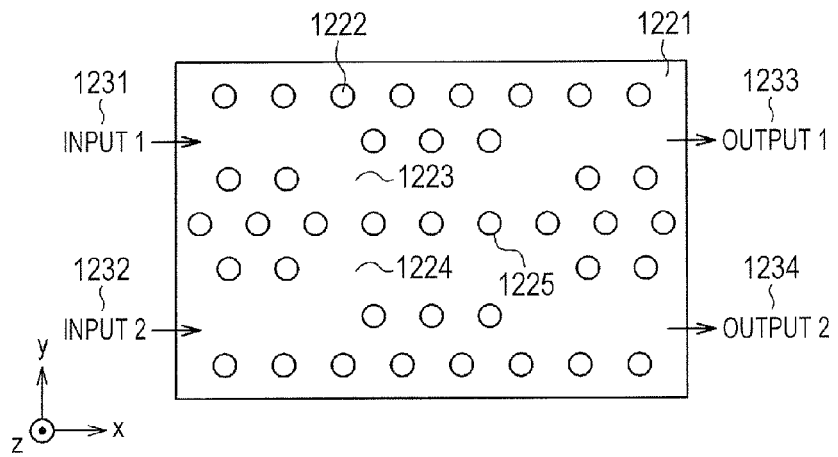
FIG. 12B is an illustration of a typical photonic crystal structure in which regions of different reflective indexes are arrayed periodically and into which two periodicity-disturbing linear regions are intentionally introduced, the two linear regions being made to function as waveguides.

FIGS. 12A and 12B are illustrations showing typical structures of photonic crystals. A photonic crystal 1201 in FIG. 12A has a structure in which regions of different refractive indexes are periodically arrayed and into which a periodicity-disturbing constitution 1204 is introduced intentionally, the photonic crystal structure thereby implementing the function of a waveguide and that of light containment. Reference numeral 1205 indicates a hollow space, and reference numeral 1211 denotes the position through which light is input. The input light is transmitted inside the hollow space 1205 before exiting via a position 1212. In the example of FIG. 12A, cavities 1203 are arrayed in a two-dimensional periodical manner on a plane 1202. Among the cavities 1203 thus arrayed, a linear region 1204 that disturbs the periodicity (a band-like region where no cavity 1203 exists) is introduced. The region 1204 functions as an optical waveguide. And in the example of a photonic crystal 1221 in FIG. 12B, periodicity-disturbing linear regions 1223 and 1224 are introduced among cavities 1222 that are likewise arrayed periodically. These linear regions function as optical waveguides. When these linear regions 1223 and 1224 are made to come close to each other halfway, interactions can be generated by near-field light or the like between the two waveguides formed by the linear regions 1223 and 1224. In this example, two input light beams 1231 and 1232 are caused to interact with each other halfway, and two light beams 1233 and 1234 are output. Cavities 1225 of a medium different from that of the other cavities may be interposed between the waveguides (linear regions) 1223 and 1224 so as to boost nonlinear optical effects.

When the refractive index and periodicity of the photonic crystal and its internal structure for disturbing the periodicity are controlled, dispersion relations such as a significant drop in group velocity of light, not available with conventional devices, can be obtained. As a result of this, it is possible to implement a device that provides strong nonlinear optical properties of three dimensions or higher such as the optical Kerr effect. By converting the light using the device offering such powerful nonlinear optical properties, the overlap between the probability distribution in effect when there is a defect and the probability distribution in effect when there is no defect can be reduced.

Whereas FIGS. 12A and 12B show typical photonic crystals having a structure in which cavities are arrayed periodically and into which a periodicity-disturbing constitution (region) is introduced, some other structure may be adopted instead as long as it provides a photonic crystal that manifests nonlinear optical properties.

Figure 13A:
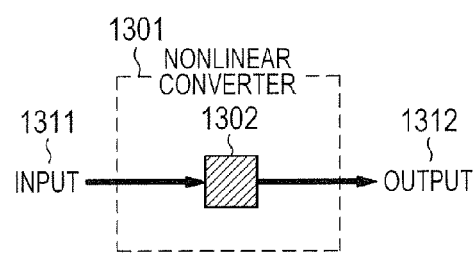
FIG. 13A is a block diagram showing a typical structure of a nonlinear transducer that uses a photonic crystal.
Figure 13B:
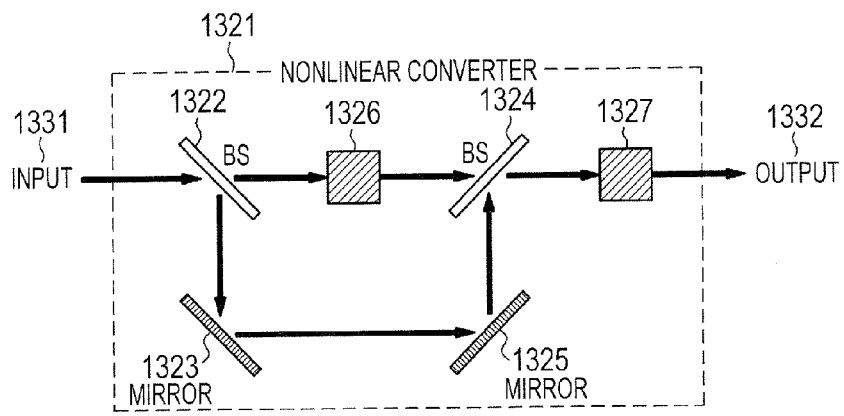
FIG. 13B is a block diagram showing a specific structure embodying a nonlinear transducer that uses a photonic crystal.

FIG. 13A is an example illustration showing a structure of a nonlinear converter that uses a photonic crystal. A nonlinear converter 1301 is a simplified example composed of a photonic crystal 1302 alone. Input light 1311 enters the photonic crystal 1302 constituting the nonlinear converter 1301 which in turn yields output light 1312 derived from nonlinear conversion. A complex nonlinear converter that includes a photonic crystal may be conceived instead. For example, a nonlinear converter 1321 shown in FIG. 13B includes two types of photonic crystals 1326 and 1327 inside. The nonlinear converter 1321 also includes beam splitters 1322, 1324 and mirrors 1323, 1325. Input light 1331 is split by the beam splitter 1322 into two light beams, one light beam being subjected to nonlinear conversion by the photonic crystal 1326 before interfering with the other light beam through the beam splitter 1324, the other light beam reaching the beam splitter 1324 after passing through an optical path formed by the mirrors 1323 and 1325. The light derived from the interference is subjected to nonlinear conversion by the other photonic crystal 1327. The nonlinear converter may have some other structure as long as it contains photonic crystals.

Figure 14:
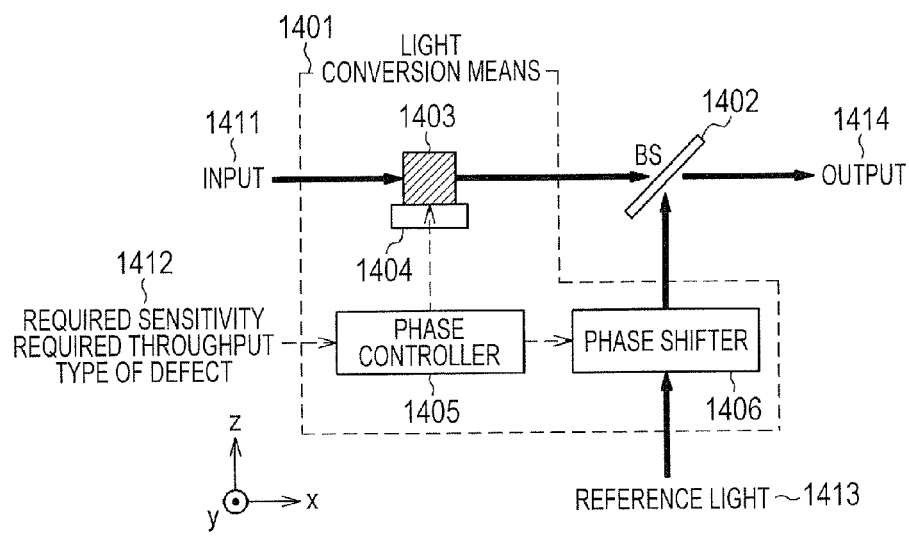
FIG. 14 is a block diagram showing a structure of light conversion means for changing the method of nonlinear conversion in accordance with required sensitivity and other factors.
Figure 15:
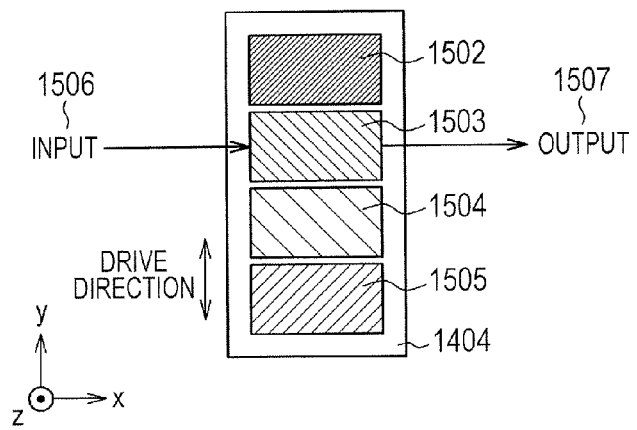
FIG. 15 is a block diagram showing the light conversion means for changing the method of nonlinear conversion in accordance with required sensitivity and other factors.

FIG. 14 shows a working example of the light conversion means for changing the method of nonlinear conversion in accordance with required sensitivity and other requirements. In this example, light conversion means 1401 includes a phase shifter 1406 that changes the phase of reference light, a device 1403 made of a plurality of types of photonic crystals, and a drive unit 1404 that drives the device 1403. Control means 1405 controls the phase shifter 1406 and drive unit 1404. While FIG. 14 is a side view of the device 1403 and drive unit 1404, FIG. 15 is a top view of these components. The device 1403 is made up of four types of photonic crystals 1502 through 1505 that can be driven by the drive unit 1404 in the y direction. The drive unit 1404 allows input light 1506 (1411) to enter one of the photonic crystals 1502 through 1505, obtaining output light 1507. Meanwhile, a beam splitter 1402 is fed with reference light 1413 whose phase is controlled during transmission through the phase shifter 1406 under control of the control means 1405 based on input information 1412 such as required sensitivity, required throughput, and defect type. The reference light 1413 interferes with the output light 1507 coming from the device 1403, and interfering light 1414 is output. In this manner, the method for nonlinear conversion of light can be controlled in accordance with required sensitivity and other requirements.

Besides the method of using different types of photonic crystals for changing the way nonlinear conversion is performed as shown in FIG. 14, other methods may be adopted to change the nonlinear optical properties of the photonic crystal. For example, a method of changing the refractive index of the photonic crystal under heat or in an electric field, a method of inserting rods into cavities of the photonic crystal, or a method of expanding and compressing the photonic crystal using a minute actuator may be utilized.

Figure 16A:
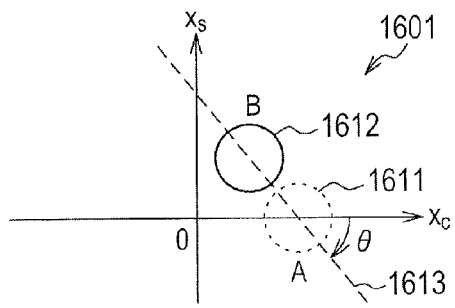
FIG. 16A is a graph as a typical phase space representation indicating the state of the target light in effect when there is a defect and the state of the target light in effect when there is no defect, without nonlinear conversion being carried out.
Figure 16B:
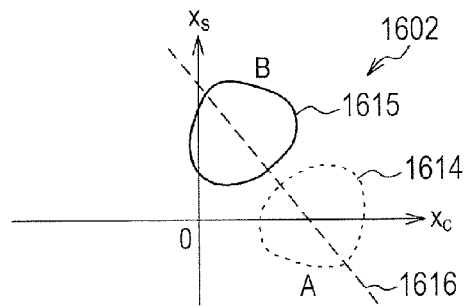
FIG. 16B is a graph as a typical phase space representation indicating the state of the target light in effect when there is a defect and the state of the target light in effect when there is no defect, with nonlinear conversion carried out.

FIGS. 16A and 16B are schematic views of phase space representations showing the state of target light in effect when nonlinear conversion is performed using the nonlinear conversion means explained in FIGS. 11A through 15. Regions 1611 and 1612 in a graph 1601 of FIG. 16A indicate the state of the target light in effect when there is no defect and when there is a defect, respectively, where nonlinear conversion is not carried out. When homodyne detection is performed, making the projection onto the axis of a straight line 1613 can reduce the overlap between the probability distributions. However, as long as nonlinear conversion is not carried out, the influence of quantum noise cannot be suppressed except by changing the direction of the projection as explained in FIG. 9.

In contrast, performing nonlinear conversion by use of the photonic crystal can suppress the influence of quantum noise. Regions 1614 and 1615 in a graph 1602 of FIG. 16B indicate the states of the target light in effect when there is no defect and there is a defect, respectively, where nonlinear conversion is carried out. Changing the shapes of the probability distributions can reduce the overlap therebetween. In this example, making the projection onto the axis of a straight line 1616 provides a higher detection rate than in a case of nonlinear conversion is not carried out. Here, it is possible to reduce the overlap between the probability distributions by changing the method of nonlinear conversion based on the phase shift amount of the reference light.

Third Embodiment

Figure 17A:
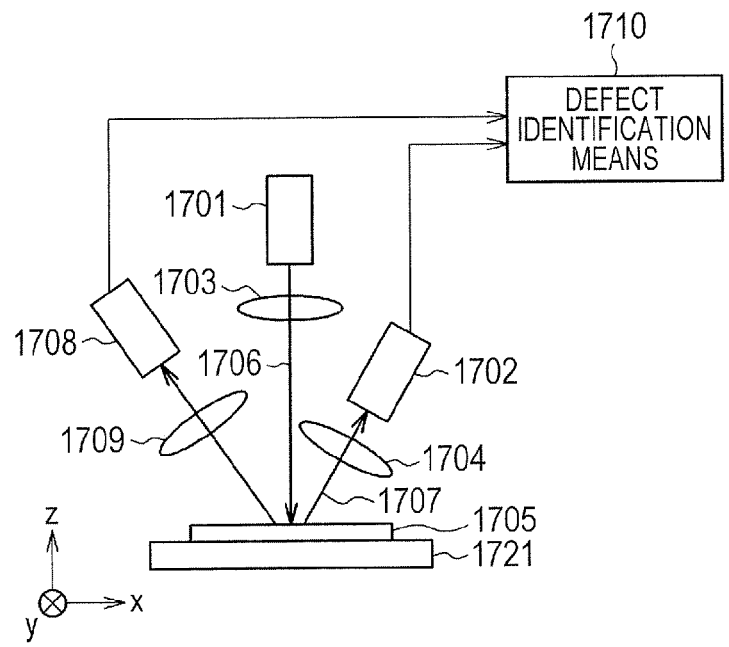
FIG. 17A is a block diagram showing a structure of an optical inspection apparatus which has a detection optical system including light interference means, light conversion means, and light detection means to be explained in conjunction with a first and a second embodiment and which detects a defect under epi-illumination.
Figure 17B:
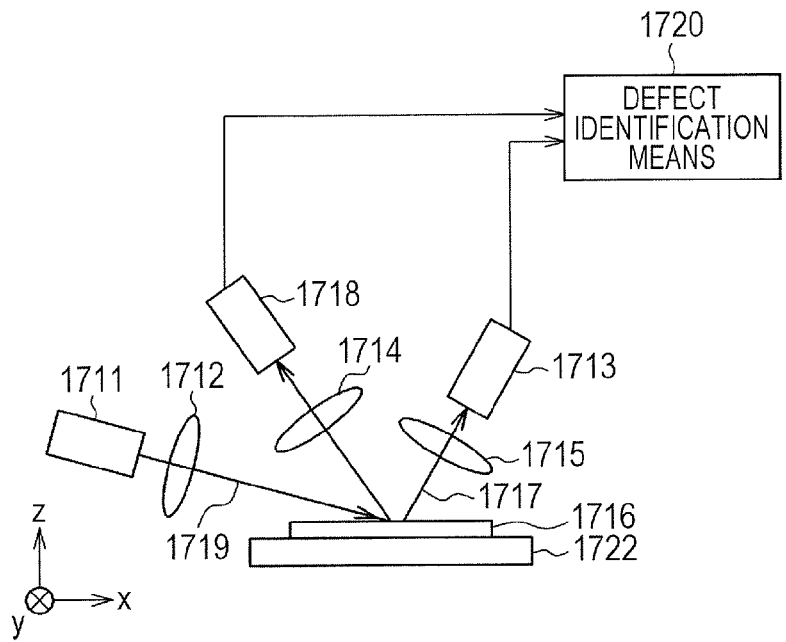
FIG. 17B is a block diagram showing a structure of an optical inspection apparatus which has the detection optical system including the light interference means, light conversion means, and light detection means to be explained in conjunction with the first and the second embodiments and which detects a defect under oblique illumination.

FIGS. 17A and 17B are illustrations showing structures of optical inspection apparatuses which include the light interference means 103 and light conversion means 103 or 306, among others, explained in conjunction with the first or the second embodiment and in which a sample is irradiated with light and the reflected light from the sample is received by the light interference means 103 and light conversion means 103 or 306.

FIG. 17A shows a structure of an inspection apparatus that irradiates a sample 1705 on a table 1721 with a light source 1701 from a perpendicular direction by epi-illumination for detection of a defect. Light 1706 emitted by the light source 1701 is focused by a lens 1703 onto the sample 1705 for epi-illumination of the sample 1705. Of the reflected light from the sample 1705, a light beam 1707 reflected in the direction of a lens 1704 is focused thereby for input to a receiver 1702. The receiver 1702 includes the light interference means (103), light conversion means (106, 306, or 1401, etc.), and light detection means (104, etc.) explained in conjunction with the first or the second embodiment. There may be provided a plurality of receivers 1702. For example, a lens 1709 and a receiver 1708 may be installed in a manner receiving scattered or reflected light in a direction different from that of the light 1707. Detection signals from the receivers 1702 and 1708 are used by defect identification means 1710 to identify the presence or absence of a defect and the type of the defect. The sample 1705 is placed on a stage 1721. Moving the stage 1721 in the x and y directions can control the light irradiation position on the sample.

FIG. 17B shows a structure in which light 1719 emitted to a sample 1716 not perpendicularly but obliquely from a light source 1711 is focused by a lens 1712 for oblique illumination. Scattered or reflected light 1717 coming from the sample 1716 toward a lens 1715 is received by a receiver 1713, and reflected light toward a lens 1714 is received by a receiver 1718. This structure allows the light to be focused onto the sample 1716 so that the light received by the receivers 1713 and 1718 may be used by defect identification means 1720 to identify information about the presence or absence of a defect at the focused position and the type of the defect.

Figure 18A:
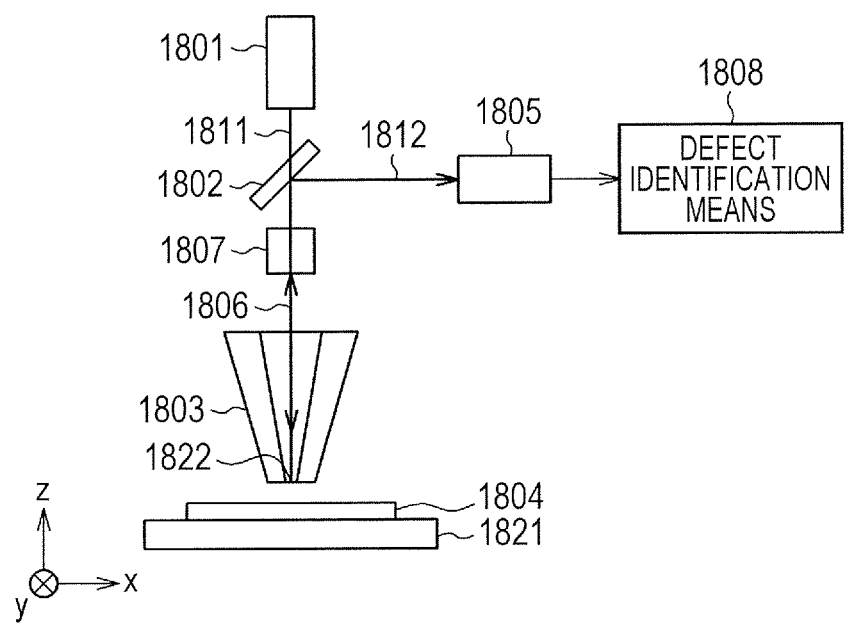
FIG. 18A is a block diagram showing a structure of an optical inspection apparatus which uses near-field light illumination means in its illumination optical system and which has the detection optical system including the light interference means, light conversion means, and light detection means to be explained in conjunction with the first and the second embodiments.
Figure 18B:
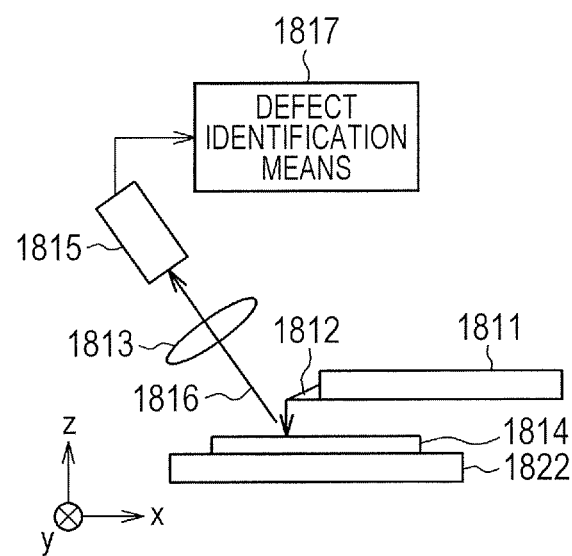
FIG. 18B is a block diagram showing a structure of an optical inspection apparatus which uses in its illumination optical system illumination means furnished with a near-field head for emitting near-field light from its tip and which has the detection optical system including the light interference means, light conversion means, and light detection means to be explained in conjunction with the first and the second embodiments.

FIGS. 18A and 18B are working example illustrations showing structures of optical inspection apparatuses, different from those shown in FIG. 17, in which a sample is irradiated with light and the reflected light from the sample is received. In the structure of FIG. 18A, the light emitted by a light source 1801 is applied to a sample 1804. Light 1811 is input to a near-field light generator 1803 whose tip 1822 releases near-field light. The near-field generator 1803 is positioned close enough to the sample 1804 so that the near-field light will reach the sample 1804. Scattered or reflected light 1812 from the sample 1804 passes through the same light path 1806 as that of the illumination light 1811 and is reflected by a beam splitter 1802 before being input to a receiver 1805. The beam splitter 1802 is arranged to let the irradiation light from the light source 1801 pass through and to reflect the light from the sample. This arrangement may be implemented, for example, by having the light from the light source 1801 polarized, positioning a ¼-wavelength plate 1807 on the light path, and installing a polarizing beam splitter as the beam splitter 1802. The receiver 1805 includes the light interference means (103), light conversion means (106, 306, or 1401, etc.), and light detection means (104, etc.) explained in conjunction with the first or the second embodiment. A detection signal from the receiver 1805 is used by defect identification means 1808 to identify the presence or absence of a defect and the type of the defect. The sample 1804 is placed on a stage 1821. Moving the stage 1821 in the x and y directions can control the light irradiation position on the sample.

FIG. 18B is an illustration showing a structure in which near-field light is applied to a sample and which differs from the structure in FIG. 18A. A near-field head 1812 and a near-field head support unit 1811 are provided. The near-field head 1812 is positioned close enough to a sample 1814 so that the near-field light released from the tip of the head 1812 will reach the sample 1814 placed on a stage 1822. Scattered or reflected light 1816 from the sample 1814 is focused by a lens 1813 for input to a receiver 1815 for light reception. An output signal from the receiver 1815 is processed by defect identification means 1817 to identify the presence or absence of a defect and the type of the defect.

Comparing with the structures described in FIGS. 17A and 17B, the structures described in FIGS. 18A and 18B make it possible to focus light onto a smaller area on the sample. This makes it possible to obtain scattered or reflected light from a minute defect at high intensity.

The invention may be embodied in other specific forms without departing from the spirit or essential characteristics thereof. The present embodiment is therefore to be considered in all respects as illustrative and not restrictive, the scope of the invention being indicated by the appended claims, rather than by the foregoing description, and all changes which come within the meaning and range of equivalency of the claims are therefore intended to be embraced therein.

DESCRIPTION OF REFERENCE NUMERALS

101 Optical inspection apparatus
102 Light irradiation means
103 Light interference means
104 Light detection means
105 Defect identification means
106 Light conversion means
111 Sample
112 Beam splitter
113 Reference light
201 Probability distribution in effect where light conversion means is not provided
202 Probability distribution in effect where light conversion means is provided
211 Probability distribution in effect when there is a defect
212 Probability distribution in effect when there is no defect
221 Overlap between probability distributions
231 Mean difference between probability distributions
301 Phase controller
302 Phase shifter

The invention claimed is:

1. An optical inspection apparatus comprising:
light irradiator which irradiates a sample with light;
reference light emitter which emits reference light;
light interference unit which generates interfering light through interference between transmitted light, scattered light, or reflected light from said sample irradiated with light by said light irradiator on the one hand, and the reference light emitted by said reference light emitter on the other hand;
light detector which detects the interfering light generated by said light interference unit;
defect identifier which identifies the presence or absence of a defect based on a detection signal obtained by said light detector detecting the interfering light; and
light convertor which converts at least the state of the transmitted light, scattered light, or reflected light from said sample, the state of the reference light emitted by said reference light emitter, or the state of the interfering light generated by said light interference unit,
wherein said light convertor converts at least the state of the transmitted light, scattered light, or reflected light from said sample, the state of the reference light emitted by said reference light emitter, or the state of the interfering light generated by said light interference unit, by adjusting the phase to reduce the overlap between probability distributions of the detection signal which is obtained by said light detector detecting said interfering light and which includes a probability distribution of defects and a probability distribution lacking defects.

2. The optical detection apparatus according to claim 1, wherein said light converter adjusts the phase of said reference light or the phase of the light irradiated by said light irradiator, in accordance with at least the required sensitivity of defect detection, required throughput, or the type of defect to be detected.

3. The optical inspection apparatus according to claim 1, wherein said light converter adjusts the phase of said reference light based on information which estimates a quantum state indicative of the state of the transmitted light, scattered light, or reflected light from said sample irradiated with light by said light irradiator, at least either when there is a defect or when there is no defect.

4. The optical inspection apparatus according to claim 1, wherein said defect identifier further acquires information about the type of defect.

\* \* \* \* \*